(12) United States Patent
Zacher

(10) Patent No.: US 11,633,275 B2
(45) Date of Patent: Apr. 25, 2023

(54) IOL INJECTOR PLUNGER HAVING IOL COMPRESSION ARMS

(71) Applicant: Alcon Inc., Fribourg (CH)

(72) Inventor: Rudolph F. Zacher, Trabuco Canyon, CA (US)

(73) Assignee: Alcon Inc., Fribourg (CH)

( * ) Notice: Subject to any disclaimer, the term of this patent is extended or adjusted under 35 U.S.C. 154(b) by 244 days.

(21) Appl. No.: 16/896,051

(22) Filed: Jun. 8, 2020

(65) Prior Publication Data

US 2020/0405475 A1    Dec. 31, 2020

Related U.S. Application Data

(60) Provisional application No. 62/867,350, filed on Jun. 27, 2019.

(51) Int. Cl.
    *A61F 2/16*      (2006.01)

(52) U.S. Cl.
     CPC ............ *A61F 2/167* (2013.01); *A61F 2/1678* (2013.01); *A61F 2002/1683* (2013.01)

(58) Field of Classification Search
     CPC . A61F 2/167; A61F 2/1678; A61F 2002/1683
     See application file for complete search history.

(56) References Cited

U.S. PATENT DOCUMENTS

| | | | |
|---|---|---|---|
| 6,022,358 A | 2/2000 | Wolf et al. | |
| 2006/0229634 A1* | 10/2006 | Shepherd | A61F 2/1667 |
| | | | 606/107 |
| 2009/0248031 A1 | 10/2009 | Ichinohe et al. | |
| 2016/0256316 A1 | 9/2016 | Van Noy et al. | |
| 2016/0270907 A1* | 9/2016 | Attinger | A61F 2/1672 |
| 2018/0368971 A1* | 12/2018 | Zacher | A61F 2/167 |
| 2020/0015957 A1* | 1/2020 | Wensrich | A61F 2/167 |
| 2020/0015959 A1* | 1/2020 | Wensrich | A61F 2/1667 |
| 2020/0197168 A1* | 6/2020 | Wu | A61F 2/1678 |
| 2020/0197169 A1* | 6/2020 | Wu | A61F 2/167 |

FOREIGN PATENT DOCUMENTS

| | | |
|---|---|---|
| EP | 0363213 A2 | 4/1990 |
| FR | 2822055 A1 | 9/2002 |

* cited by examiner

*Primary Examiner* — Jerrah Edwards
*Assistant Examiner* — Aren Patel
(74) *Attorney, Agent, or Firm* — Patterson + Sheridan, LLP

(57) ABSTRACT

An IOL injector plunger having IOL compression arms is described.

11 Claims, 12 Drawing Sheets

IOL INJECTOR PLUNGER HAVING IOL COMPRESSION ARMS

CROSS-REFERENCE TO RELATED APPLICATION

This application claims priority to and benefit of U.S. Provisional Patent Application No. 61/867,350, filed Jun. 27, 2019. The entire contents of each of which are incorporated by reference herein in their entirety.

TECHNICAL FIELD

The present disclosure relates to systems, apparatuses, and methods for intraocular lens (IOL) injectors.

BACKGROUND

The human eye in its simplest terms functions to provide vision by transmitting and refracting light through a clear outer portion called the cornea, and further focusing the image by way of the lens onto the retina at the back of the eye. The quality of the focused image depends on many factors including the size, shape, and length of the eye, and the shape and transparency of the cornea and lens. When trauma, age, or disease cause the lens to become less transparent, vision deteriorates because of the diminished light which can be transmitted to the retina. This deficiency in the lens of the eye is medically known as a cataract. The treatment for this condition is surgical removal of the lens and implantation of an artificial lens (IOL).

Many cataractous lenses are removed by a surgical technique called phacoemulsification. During this procedure, an opening is made in the anterior capsule of an eye and a phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced with an IOL.

The IOL may be injected into the eye through a small incision, sometimes the same incision used to remove the diseased lens. An IOL injector may be used to deliver an IOL into the eye.

SUMMARY

An intraocular lens (IOL) injector plunger is described. The plunger has a plunger tip formed at a distal end of the plunger and adapted to contact an IOL and axially move the IOL in response to an axial force applied to the plunger. The plunger also has a first and a second flexible IOL compression arm disposed on opposite lateral sides of the distal end of the plunger, each compression arm having a proximal end coupled to the plunger, and a tapered distal end forming a compression arm tip. In an initial compression arm configuration, the compression arms are laterally splayed such that the first compression arm tip is adapted to contact a first end of a proximal haptic of an uncompressed IOL, the first end comprising a haptic tip of the proximal haptic. In the initial compression arm configuration, a second compression arm tip is adapted to contact a second end of a proximal haptic of an uncompressed IOL. In response to inward lateral forces applied to outer lateral surfaces of the compression arms, the compression arms are adapted to flex toward one another to adopt a second compression arm configuration wherein the compression arms are adapted to apply an inward lateral force onto an IOL, and thereby guide the IOL to adopt a compressed configuration.

The plunger tip may be adapted to contact the IOL in response to the IOL adopting the compressed configuration.

The plunger may be disposed within an injector body of an IOL injector. The injector body may include a main body having a proximal end and a distal end, a nozzle having a proximal end and a distal end, the proximal end of the nozzle coupled to the distal end of the main body. The nozzle may include an IOL storage location configured to house an uncompressed IOL, and an IOL dwell location distal to the IOL storage location. The injector body may include a bore having a longitudinal axis extending from the proximal end of the main body to the distal end of the nozzle, wherein a distal portion of the bore within the nozzle forms a tapered delivery channel. The plunger may be movably coupled within the injector body and aligned within the bore. In response to an axial movement of the plunger, each of the compression arms may be adapted to move axially and contact an internal lateral surface of the tapered delivery channel, and in response, the compression arms may be adapted to flex toward one another to adopt a second compression arm configuration wherein the compression arms are adapted to apply an inward lateral force onto an IOL, and thereby guide the IOL to adopt a compressed configuration.

The compression arms may be configured to be decoupled from the plunger in response to the compression arms adopting the second configuration. In response to decoupling, upon further axial movement of the plunger, the compression arms may be adapted not to further move axially within the delivery channel, and the plunger tip may be adapted to axially push a compressed IOL through the delivery channel.

The proximal ends of the compression arms may each include a pin, and the plunger may include a hole adapted to receive the pins, thereby coupling the compression arms to the plunger. A portion of the distal end of the main body may include a sleeve having a bore sized such that the pins are adapted to be disposed within the hole when the proximal ends of the compression arms axially are disposed within the sleeve. The compression arms may be adapted such that, in response to the compression arms moving from the initial compression arm configuration to the second compression arm configuration, the proximal ends of the compression arms are adapted to exit the sleeve and in response are adapted to flex outward away from the plunger, thereby removing the pins from the hole and decoupling the compression arms from the plunger.

The delivery channel may include a hard stop adapted to contact the compression arm tips and prevent the decoupled compression arms from further axially moving through the delivery channel.

The nozzle may include channels disposed longitudinally within the nozzle and adapted to receive the compression arms. In response to axial movement of the plunger following compression of the IOL, a portion of the compression arms may be configured to be decoupled from the plunger such that the plunger tip is adapted to axially move through the delivery channel, and the compression arms may be adapted to axially slide through the channels.

The IOL may be in the IOL storage location when the compression arms are in the initial compression arm configuration, and the IOL is in the dwell location when the compression arms are in the second compression arm configuration.

The compression arms may have a concave inner surface adapted to contact a lateral outer edge of an IOL and a lower outer edge of an IOL.

The IOL injector may be adapted to separately inject an IOL base, an IOL optic, or both.

The IOL injector may be adapted to concurrently inject an IOL base and an IOL optic.

BRIEF DESCRIPTION OF THE DRAWINGS

For a more complete understanding of the present disclosure, reference is now made to the following description, taken in conjunction with the accompanying drawings, which are not to scale, and in which.

DETAILED DESCRIPTION

Figure 1:
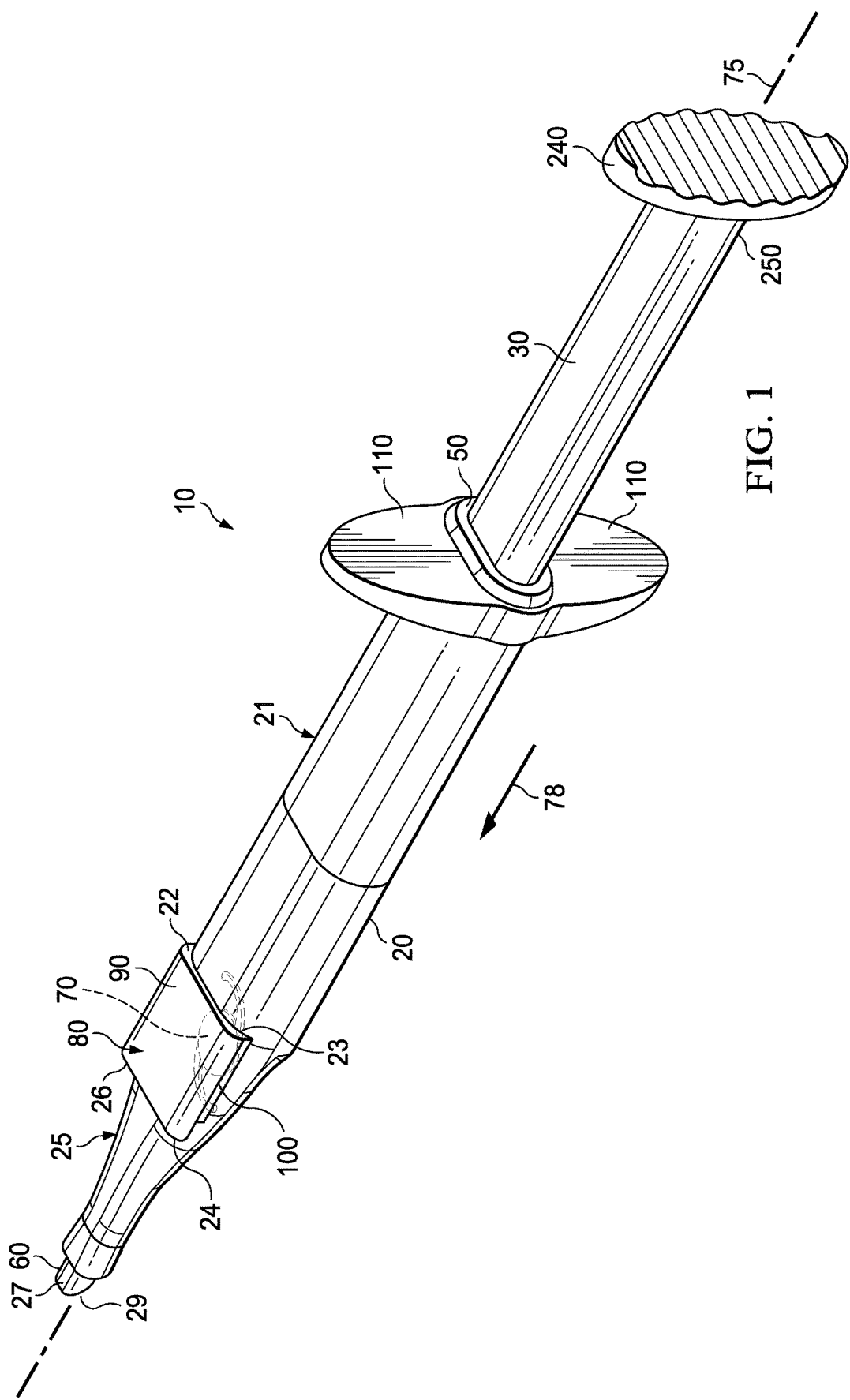
FIG. 1 is a perspective view of an example IOL injector.

For the purposes of promoting an understanding of the principles of the present disclosure, reference will now be made to the implementations illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

Figure 2:
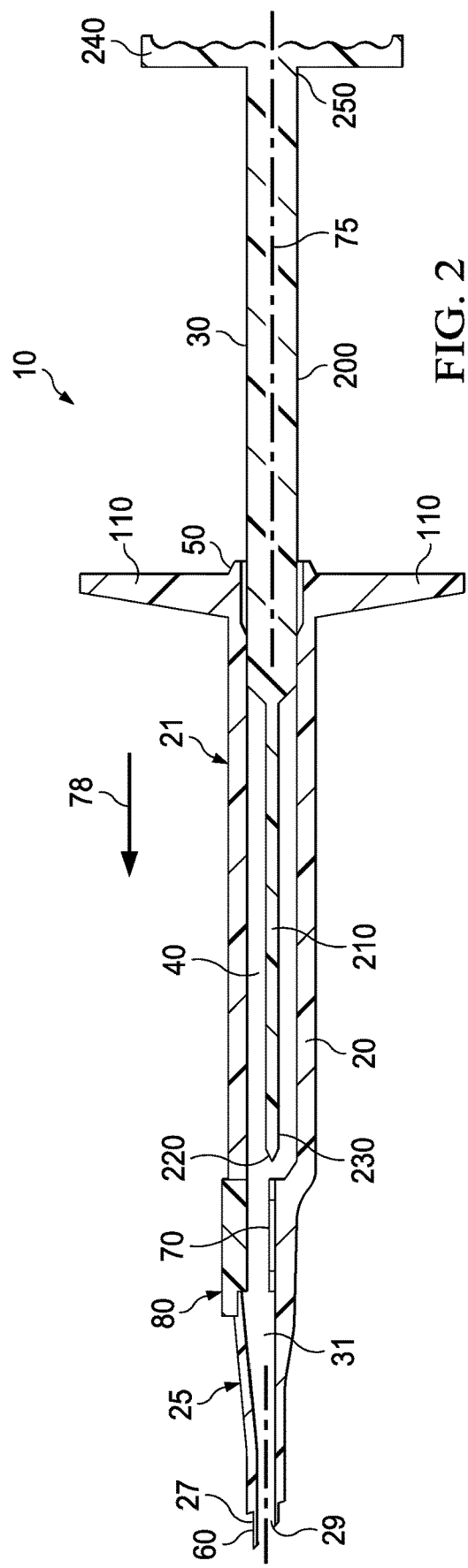
FIG. 2 is a longitudinal cross-sectional view of the example IOL injector of FIG. 1.

FIGS. 1 and 2 are schematics of an example IOL injector 10 that is actuated by manual user application of force. The IOL injector 10 includes an injector body 20, a plunger 30 adapted to reciprocate through a bore 40 formed in the injector body 20. The injector body 20 has a main body 21 having a proximal end 50 and a distal end 23, and a nozzle 25 having a proximal end 22 and a distal end 60. The proximal end 22 of the nozzle 25 is coupled to the distal end 23 of the main body 21. The nozzle 25 has an IOL storage location 80 configured to house an uncompressed IOL 70, and an IOL dwell location 809 distal to the IOL storage location 80.

The bore 40 extends from the proximal end 50 of the main body 21 to the distal end 60 of the nozzle 25. A distal portion of the bore 40 within the nozzle 25 forms a tapered delivery channel 31 through which an IOL may be axially advanced, compressed, and delivered into an eye via an opening 29 in distal tip 27 at distal end 60.

The plunger 30 is movably coupled within the injector body 20 and aligned within the bore 40. The plunger 30 has a plunger tip 220 adapted to contact an IOL 70.

The IOL injector 10 also includes a longitudinal axis 75. The longitudinal axis 75 may extend along the plunger 30 and define a longitudinal axis of the plunger 30.

The IOL storage location 80 may include a door 90 to provide access to the interior of the IOL storage location 80. The door 90 may include a hinge 100 such that the door 90 may be pivoted about the hinge 100 to open the IOL storage location 80 and, for example, allow the installation of the IOL 70. In other implementations, the IOL storage location 80 may exclude a door for installing the IOL 70. In such instances, the IOL 70 may be incorporated into the IOL storage location 80 at the time of assembly of the IOL injector 10. Thus, in such instances, the IOL injector 10 would be a preloaded IOL injector. In such instances, the IOL storage location 80 may have a cover that is not configured to open, rather than a door 90. The IOL storage location 80 may include a hole adapted to allow addition of viscoelastic into the IOL storage location 80.

The injector body 20 may also include tabs 110 formed at the proximal end 50 of the injector body 20. The tabs 110 may be manipulated by fingers, thumb, or hand of a user, such as an ophthalmologist, an ophthalmic surgical assistant or nurse, or other medical professional, to advance the plunger 30 through the bore 40.

The plunger 30 may include a plunger body 200, a plunger rod 210 extending distally from the plunger body 200, and a plunger tip 220 formed at the distal end 230 of the plunger rod 210 and adapted to contact an IOL disposed, for example, with the IOL storage location 80 of the IOL injector 10. As the plunger 30 is axially advanced and thereby displaced distally within the bore 40 in the direction of the arrow 78, the plunger tip 220 of the plunger 30 is adapted to engage and advance the IOL, such as IOL 70. In FIGS. 1 and 2, the IOL 70 is shown located within the IOL storage location 80. The plunger 30 may also include flanges 240 formed at proximal end 250, which may be manipulated by the fingers, thumb, or hand of a user to advance the plunger 30 through the bore 40 by displacing the plunger 30 through the bore 40 distally in the direction of the arrow 78.

Figure 3A:
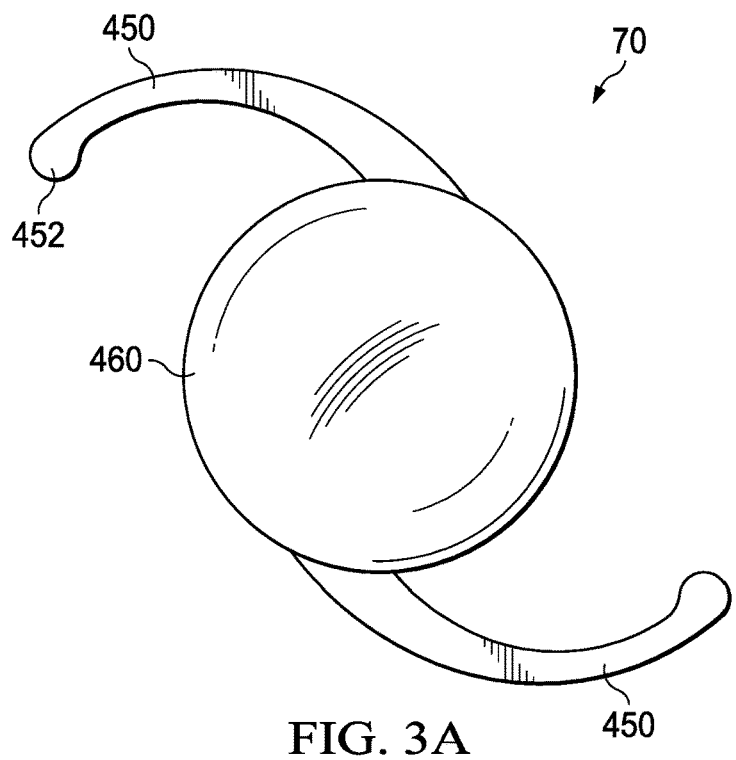
FIG. 3A shows an example one-piece IOL.

In some implementations, the IOL 70 may be a one-piece IOL. That is, in some implementations, the IOL 70 may include an optic 460 and haptics 450, as shown in FIG. 3A. Each of the haptics 450 include a tip 452. In some implementations, the optic 460 and the haptics 450 may be integrally formed out of a single piece of material. In other implementations, the optic 460 may be formed out of one piece of material; the haptics 450 may be formed out of another piece of material, and the optic 460; and the haptics 450 may be coupled together prior to delivery into an eye. In some instances, the optic 460 and haptics 450 may be fixedly secured to each other prior to insertion into an IOL injector and delivered into an eye.

Figure 3B:
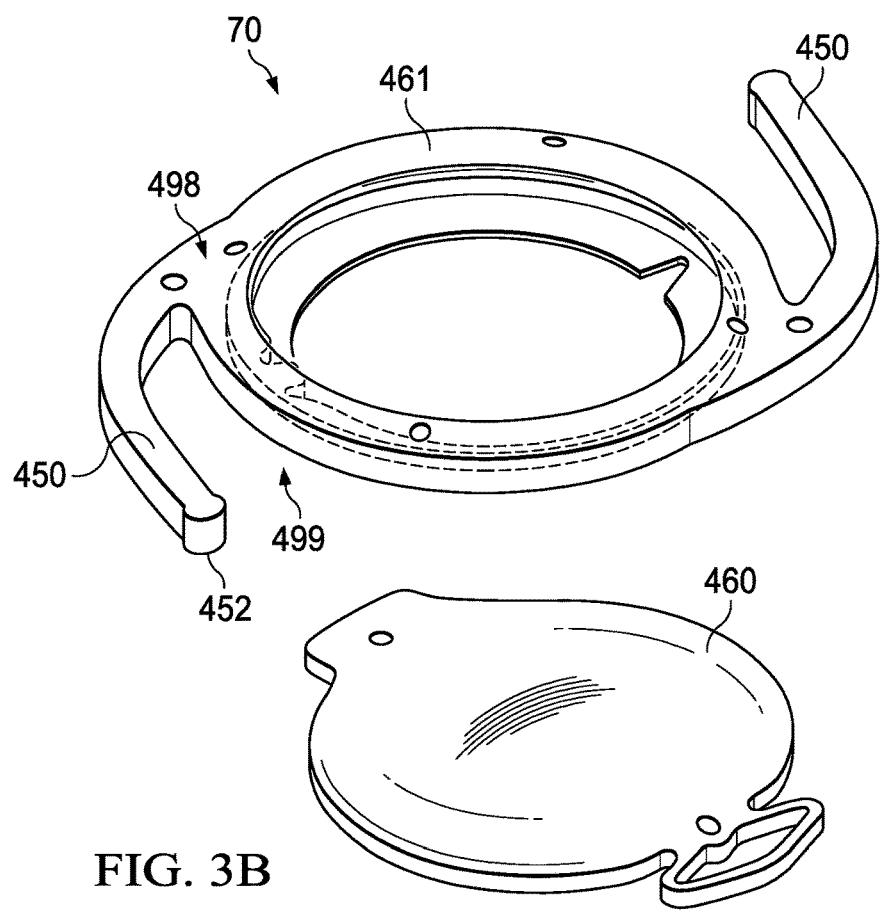
FIG. 3B shows an example two-piece IOL including a base and an optic.
Figure 4:
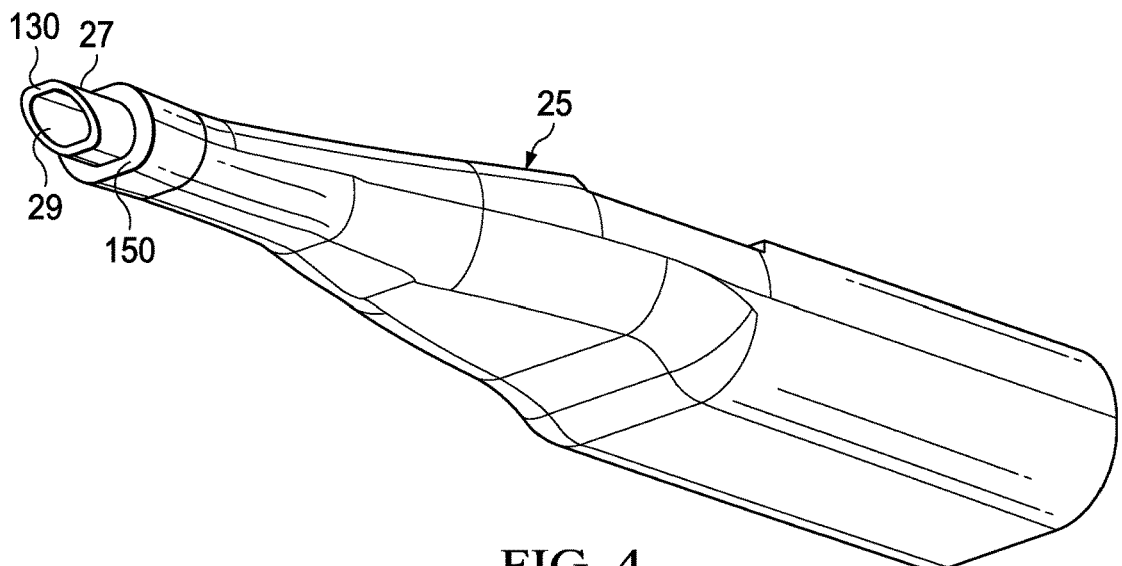
FIG. 4 is a perspective view of an example nozzle of an IOL injector.
Figure 5A:
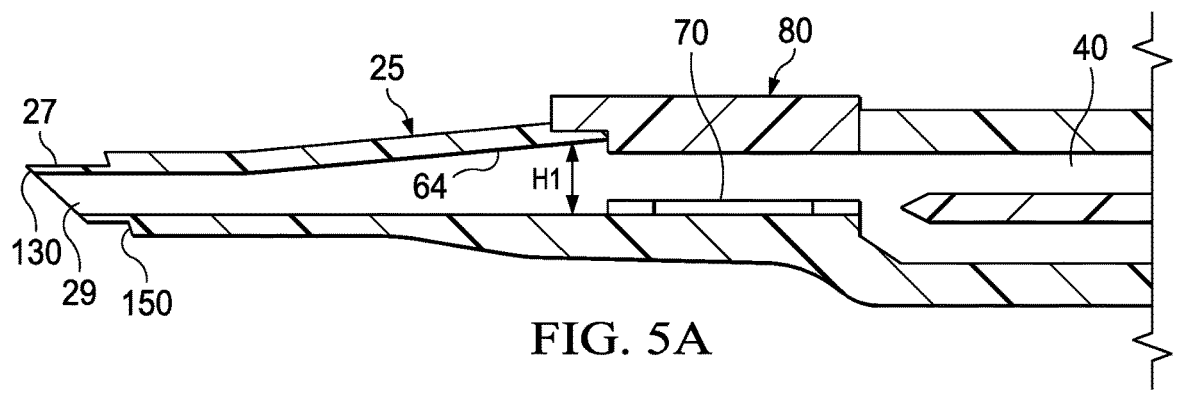
FIG. 5A is a cross-sectional view of the nozzle of the IOL injector of FIG. 4.
Figure 5B:
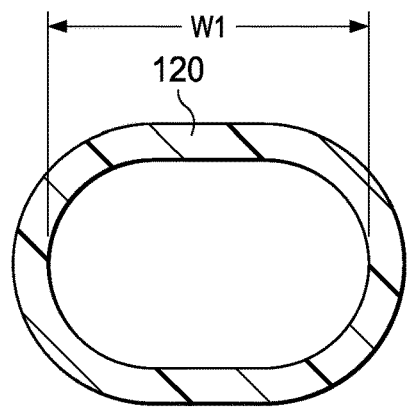
FIG. 5B is another cross-sectional view of the nozzle of the IOL injector of FIG. 4.

In other implementations, the IOL 70 may be a multi-piece IOL, as shown, for example, in FIG. 3B. For example, in some implementations, the IOL 70 be include two or more separate components. FIG. 3B is an example IOL 70 that includes two removably attached components. As shown in FIG. 3B, the IOL 70 includes an optic 460 and a base 461 that includes haptics 450 and that has a top 498 and a bottom 499. The optic 460 and the base 461 are adapted to be coupled together into a unitary IOL and, thereafter, detached from each other into separate components, if desired. In some instances, one or more components of a multi-piece IOL, such as, for example the two-piece IOL 70 shown in FIG. 3B, are separately injectable into a patient's eye. Once in the eye, the components may be assembled into a complete IOL. For example, in the case of the two-piece IOL 70 shown in FIG. 3B, the optic 460 and the base 461 are separately injectable into an eye. Once injected, the optic 460 is adapted to be coupled to the base 461 within the groove 14 disposed within an inner edge 8 of the base 461.

Occasionally, patients may require replacement of an IOL, and a procedure to replace an IOL may result in damage to the eye. With the use of a two-piece IOL, for example, a replacement procedure may involve replacement only of the optic, allowing the base to remain in place within the eye.

As explained above, in some implementations, the IOL 70 may be a two-piece IOL wherein the base 461 and the optic 460 are separately injected into the patient's eye. Accordingly, for two-piece IOLs, the base 461 and the optic 460 may be contained in separate IOL injectors 10 for insertion in the eye. In other implementations, the two components of a two-piece IOL may be inserted into an eye separately using a single IOL injector. For a single piece IOL, the optic 460 and haptics 450 form a unitary IOL and are inserted into an eye simultaneously with the use of a single IOL injector.

Accordingly, in some implementations, a user may place a one-piece IOL into an IOL injector, for example, by loading an IOL into an IOL storage compartment of the IOL injector, such as the IOL storage location 80 of the IOL injector described above. As also explained, the IOL storage location 80 may be accessed via a door, such as the door 90.

In the case of a two-piece IOL, in some implementations, a user may load the base, such as base 461, into an IOL storage compartment of an IOL injector, for example, via a door. The optic such as optic 460, may be introduced into the IOL storage compartment of a separate IOL injector, for example, via a door. In some instances, the IOL storage compartment may be accessed through the door such as door 90.

In some implementations, the IOL may be pre-loaded into the storage compartment of an IOL injector, for example, during manufacturing or otherwise prior to distribution to an end user. Accordingly, for the one-piece IOL, the one-piece IOL may be pre-loaded into the storage compartment an IOL injector prior to receipt by the end user. For a two-piece IOL, the base may be pre-loaded into a storage compartment of one IOL injector, while the optic may be pre-loaded into the IOL storage compartment of another IOL injector. The term "pre-loaded" as used herein means that an IOL, either in a one-piece or multi-piece configuration (including, for example, a two-piece configuration) is loaded into the IOL injector not by a user, but, rather, the IOL is installed in the IOL injector before and is already contained within the IOL injector when the IOL injector is received by the user. The IOL injector(s) may be packaged within sterile packaging when received by a user.

As would be understood by persons of ordinary skill in the art upon reading the present disclosure, an IOL that is pre-loaded into an IOL injector has advantages over manual installation and folding of an IOL into the IOL injector that is performed by a user. For example, manual installation and folding of an IOL may allow more opportunity for errors, which have the potential to cause unnecessary secondary manipulation or correction during an already complex procedure. For example, manual installation and folding of an IOL may also introduce the possibility of contamination of the IOL, such as by human error or poor sterile technique. Contamination of the IOL may compromise the sterile environment for the patient and risk infection or other harm to the patient.

FIGS. 4-7 illustrate details of the example nozzle 25. In some instances, the nozzle 25 has a tapered exterior surface. Further, the nozzle 25 may include a portion of the bore 40 forming a tapered delivery channel 31 that tapers towards the opening 29. The distal tip 27 is adapted for insertion into an eye so that the IOL 70 may be implanted. The IOL 70 is expelled from the opening 29 formed in the distal tip 27 into the eye. As shown in FIG. 5B, tapered delivery channel 31 and the distal tip 27 may have an elliptical cross section 120 having a width W1. Additionally, the distal tip 27 may include a beveled tip 130. The IOL storage location 80, delivery channel 31, and opening 29 may define a delivery passage. A size of the delivery passage may vary along its length. For example, in some instances, the width W1, a height H1, or both, of the delivery passage may change along a length of the delivery passage. The variation in size of the delivery passage may contribute to the compression of the IOL as it is advanced therealong through the delivery passage.

In some instances, the injector body 20 may include an insertion depth guard 140. The insertion depth guard 140 may form a flanged surface 150 that is adapted to abut an exterior eye surface. The insertion depth guard 140 abuts an eye surface and, thereby, limits an amount by which the distal tip 27 is permitted to extend into an eye, as described in U.S. application Ser. No. 15/049,315, the disclosure of which is being incorporated herein by reference in its entirety.

Figure 6:
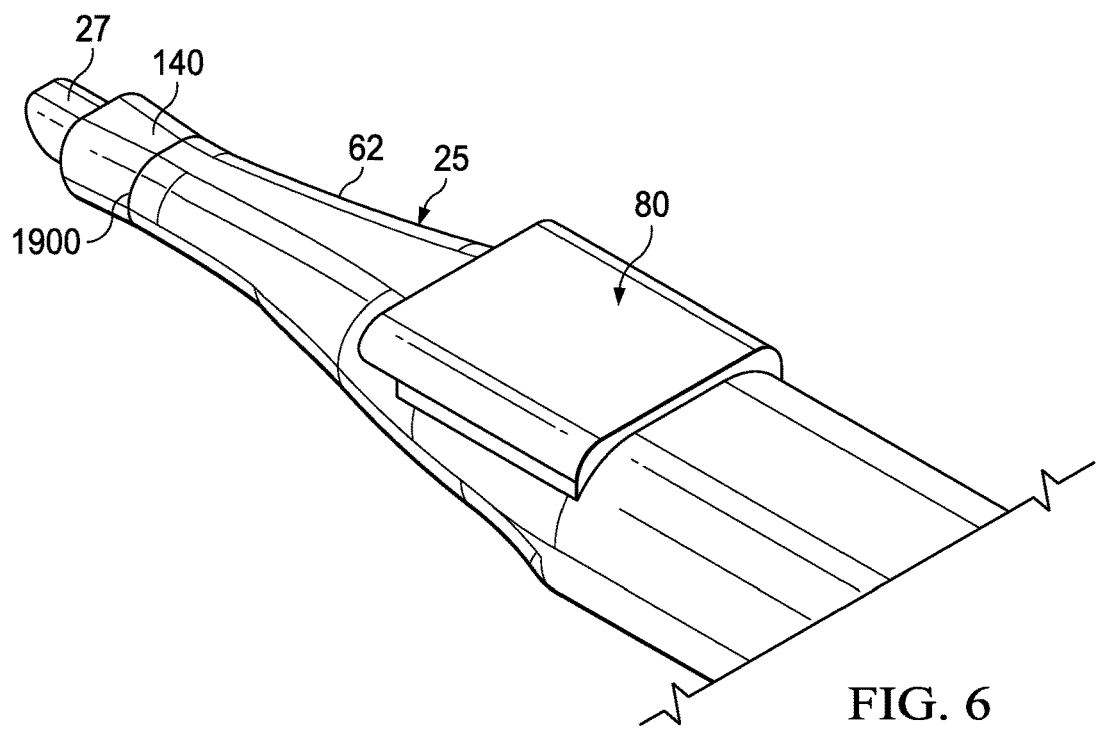
FIG. 6 is another perspective view of the nozzle of the IOL injector of FIG. 4.
Figure 7:
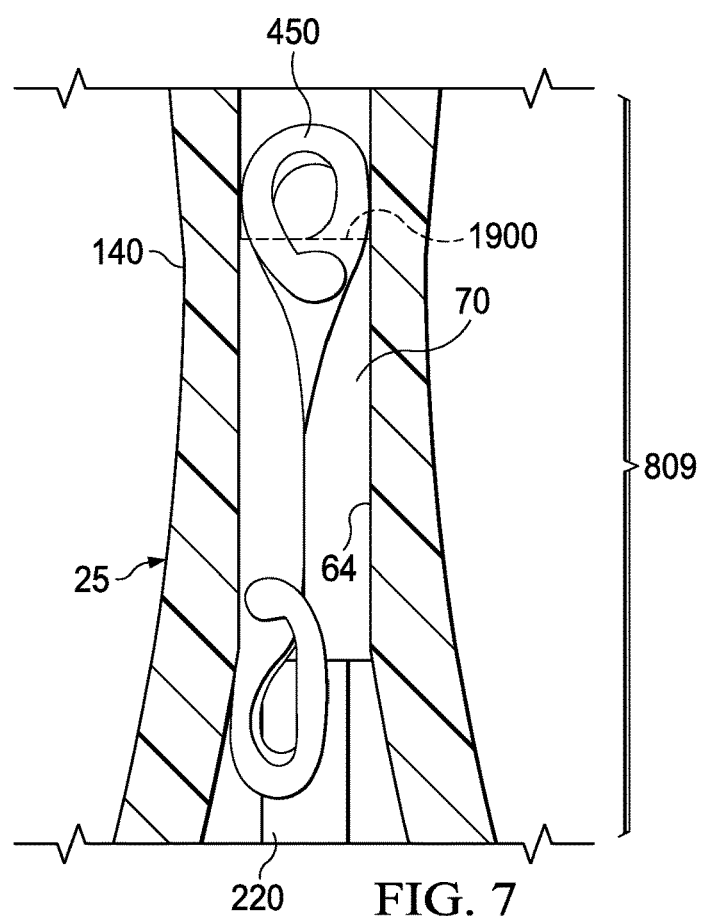
FIG. 7 is a view of a distal end of an example IOL injector with an IOL located therein and positioned in a dwell location.

FIG. 6 and FIG. 7 are detail views of a portion of the example nozzle 25. The nozzle 25 may include a tapered portion 62 and the insertion depth guard 140. The distal tip 27 may include a demarcation 1900 that provides a visual indication of a dwell location 809 of a compressed or partially compressed IOL 70. The term "dwell location" as used herein refers to a location adjacent to the distal end 60 of the nozzle 25. For example, the dwell location 809 may be a location 2-10 mm from the distal end 60. For example, in the example shown in FIG. 6, the demarcation 1900 is a narrow ridge or line that encircles all or a portion of the nozzle 25. In some instances, the demarcation 1900 may be disposed between the tapered portion 62 and the insertion depth guard 140. At least a portion of the injector body 20 may be formed from a transparent or semi-transparent material that permits a user to see an IOL within the injector body 20. Particularly, the nozzle 25 of the injector body 20 may be formed from a transparent material to permit observation of the IOL as it is moved therethrough by the plunger 30.

FIG. 7 shows a view of the distal end 60 of the IOL injector 10 with an IOL 70 located therein at a dwell location 809 in nozzle 25. As shown in FIG. 7, the dwell location 809 of the IOL 70 may be defined as a location where a distal edge of the optic of the IOL 70 substantially aligns with the demarcation 1900. A haptic 450 or a portion thereof may extend beyond the demarcation 1900.

In various implementations described herein, the IOL injector 10 includes a plunger 30 adapted to have an increased surface area of contact with an IOL 70. In particular, in some implementations the plunger 30 described herein has a wide distal end adapted to contact an uncompressed IOL 70 and collapse the IOL 70 under control, such that the IOL 70 is able to be compressed into a narrow configuration for delivery through the nozzle 25 of the IOL injector 10. In certain implementations, the plunger 30 described herein is configured to distribute axial load such that the IOL 70 is prevented from "bunching" upon plunger advancement.

The term "bunching" as used herein refers to unwanted axial folding or compression in the longitudinal axis of an IOL 70 that may sometimes occur when a traditional plunger is used to advance the IOL 70 through the delivery channel of an IOL injector. Traditional plungers typically have a single point of contact with an IOL having a relatively small IOL contact surface area or having a plunger tip that contacts a relatively small portion of an IOL circumference. Typical plungers have a plunger tip that contacts only about 5% of an IOL circumference. In particular, bunching may sometimes occur when using a traditional plunger to advance an IOL 70 through the nozzle 25, such as within the tapered delivery channel 31, for example from a storage location 80 to a dwell location 809, and/or such as when advancing an IOL 70 from a portion of the bore 40 having a relatively larger height H1 and/or width W1 into a narrower portion such as in the tapered delivery channel 31.

In contrast with typical hard-tipped plungers described above, some other existing plungers, for example collapsible, elastomeric plungers have soft-tips, such as silicone soft-tipped plungers. Typical soft-tipped plungers have a plunger tip that contacts about 10-15% of an IOL circumference. However, soft-tipped plungers have disadvantages such as high resistance of the elastomeric material against the interior surface of the delivery channel 31, and a tendency of the silicone to deform unpredictably.

Accordingly, in certain implementations, the plunger 30 described herein utilizes a different principle of operation from that of traditional plungers or other existing plungers, which typically only have a single point of contact with an IOL having a relatively small IOL contact surface area or IOL circumference, and are typically configured only to axially push an IOL through a bore 40 of an injector body 20.

Figure 8:
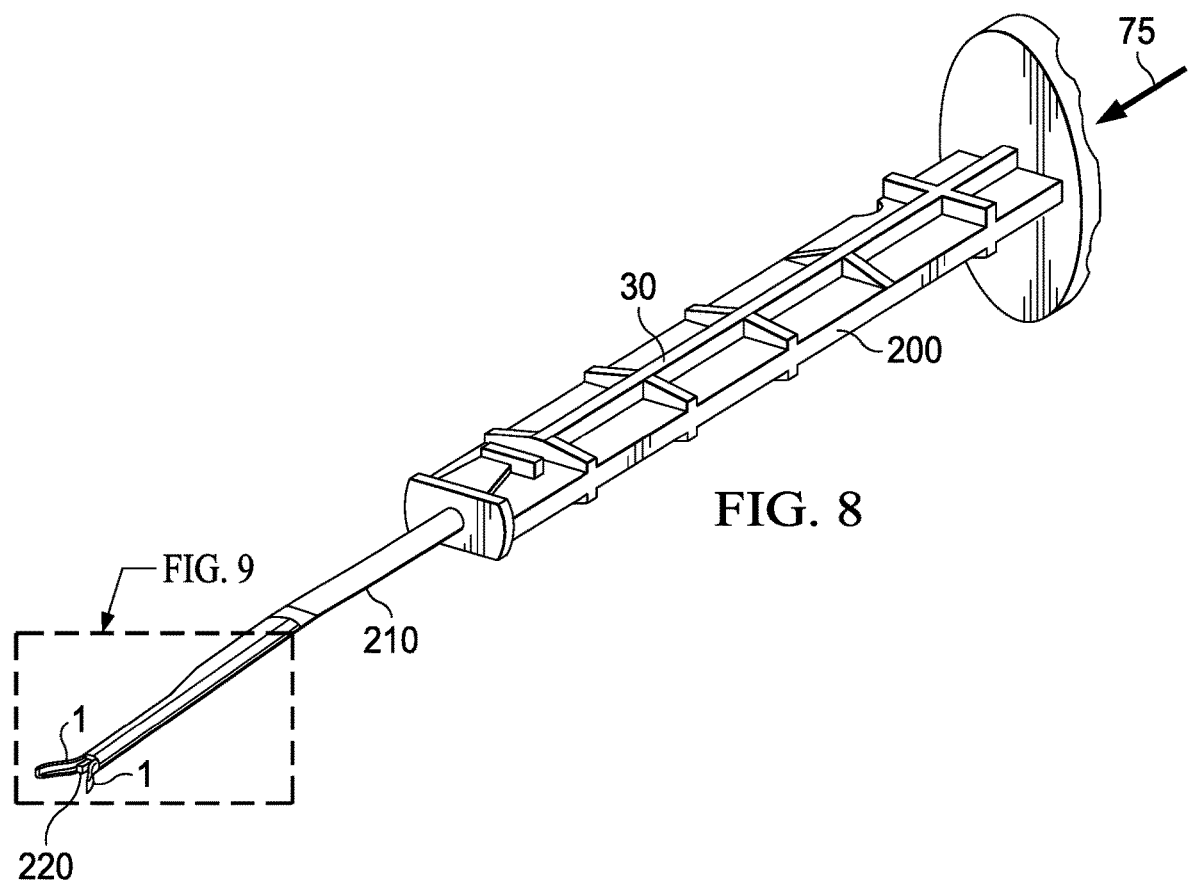
FIG. 8 is a perspective view of an example plunger having IOL compression arms.
Figure 9:
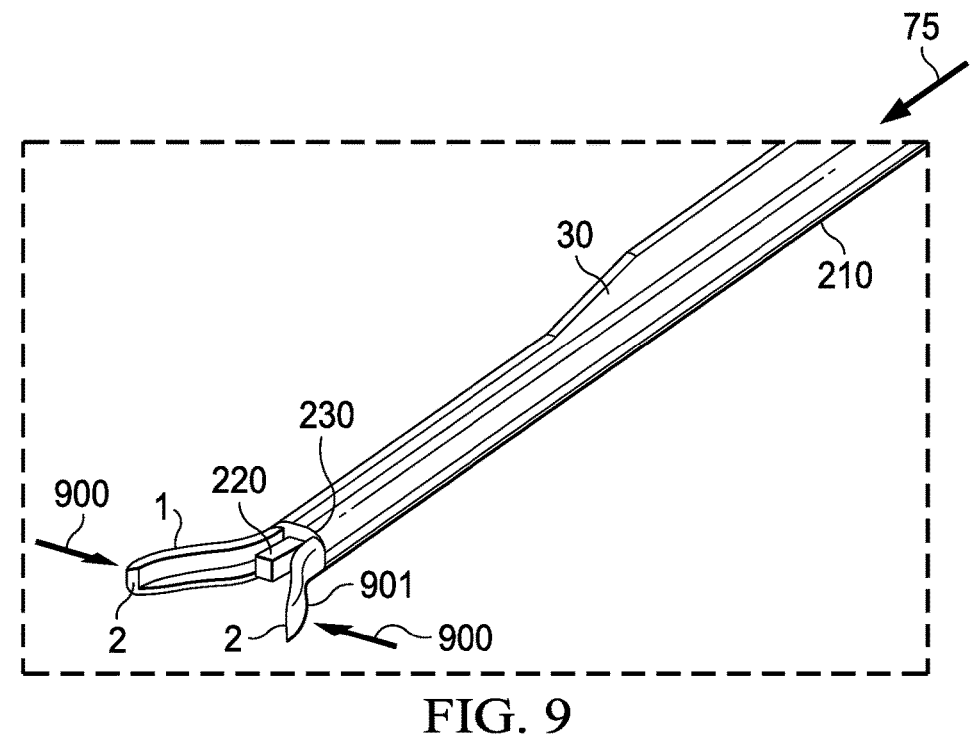
FIG. 9 is another perspective view of an example plunger having IOL compression arms.

FIG. 8-FIG. 9 are schematics of an example plunger 30 of the present disclosure having compression arms 1 adapted to provide lateral, inward squeezing force onto the IOL 70, concurrent with an axial force applied to advance the IOL 70 through the nozzle 25.

In implementations described herein, the plunger 30 has a plunger tip 220 formed at the distal end 230 of the plunger, such as at the distal end 230 of the plunger rod 210, and adapted to contact an IOL 70 and axially move the IOL 70 in response to an axial force applied to the plunger 30, and in addition, one or more compression arms 1. Typically, the plunger 30 described herein has a first and a second flexible IOL compression arm 1 disposed on opposite lateral sides of the distal end 230 of the plunger 30. Each of the compression arms has a proximal end coupled to the plunger 30, such as coupled to the distal end 230 of the plunger rod 210, and a distal end, such as a tapered distal end, forming a compression arm tip 2. The compression arms described herein are adapted to provide an increased surface area of contact with an IOL. The compression arms 1 provide various advantages, including, for example, the ability to laterally collapse or compress an uncompressed IOL 70 under control, such that it is able to be compressed into a narrow configuration for delivery through the nozzle 25. Together, the plunger tip 220 and the compression arms 1 may form a wide IOL contact surface area. For example in some implementations, the plunger having compression arms may be adapted to contact, or contact about, 25% of an IOL circumference.

In an initial compression arm 1 configuration, the compression arms 1 may be laterally splayed such that the first compression arm tip 2 is adapted to contact a first end of a proximal haptic 450 of an uncompressed IOL, the first end comprising a haptic tip 452 of the proximal haptic 450, and a second compression arm tip 2 is adapted to contact a second end of the proximal haptic 450 of an uncompressed IOL 70.

The term "splayed" as used herein refers to a configuration wherein the compression arms tips 2 point away from each other, such that the compression arms 1 are disposed relative to each other at an angle, for example, of at least 10°, at least 20°, at least 30°, at least 40°, or at least 50°.

Figure 10A:
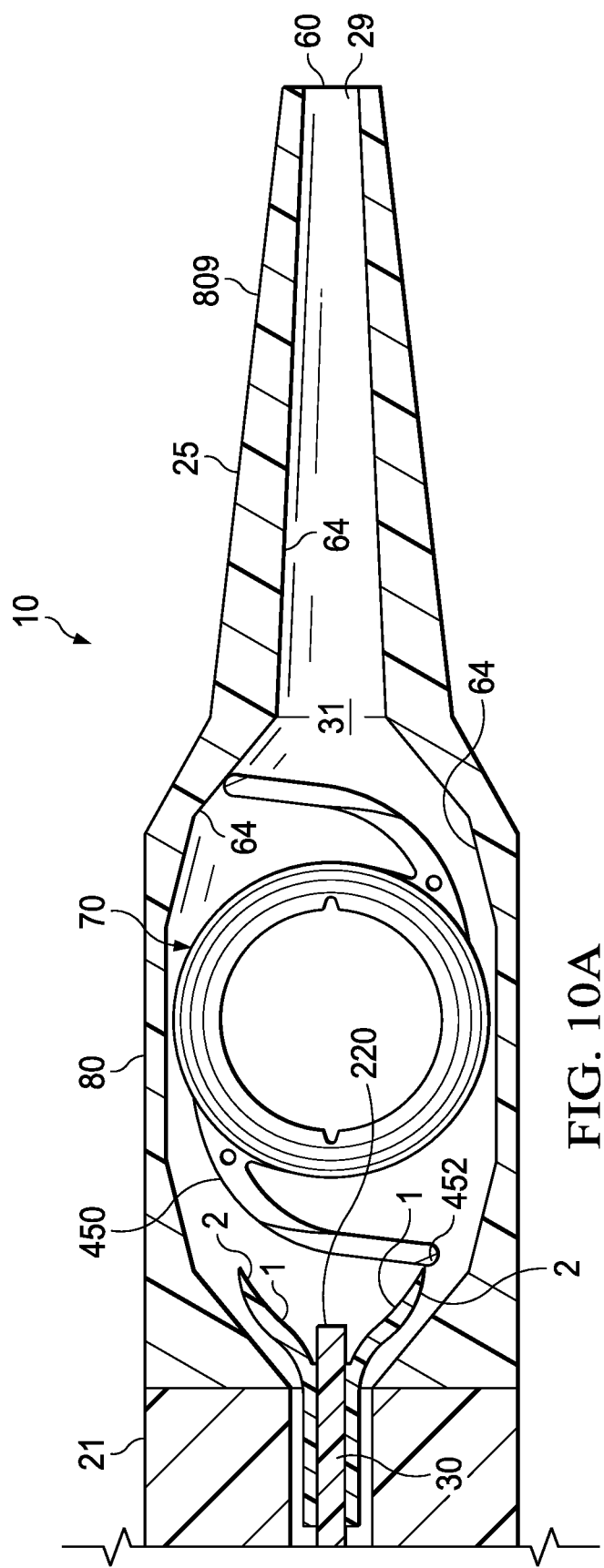
FIG. 10A is a schematic of an example plunger having IOL compression arms in an initial compression arm configuration, and an uncompressed IOL 70, disposed within an IOL injector.
Figure 10B:
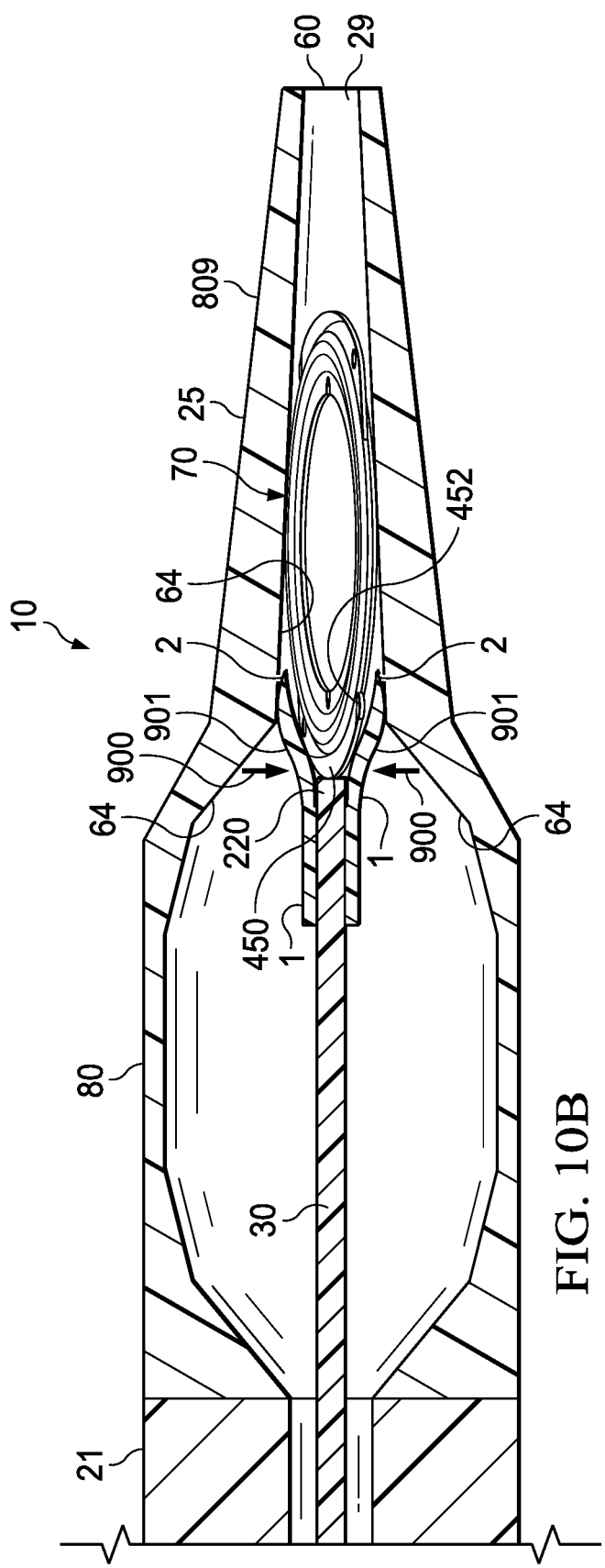
FIG. 10B is a schematic of an example plunger having IOL compression arms in a second compression arm configuration, and a compressed IOL 70, disposed within an IOL injector.

In response to inward lateral forces, such as in the direction of arrows 900, in FIG. 9 and FIG. 10B, applied to outer lateral surfaces 901 of the compression arms 1, the compression arms 1 are adapted to flex toward one another to adopt a second compression arm 1 configuration wherein the compression arms 1 are adapted to apply an inward lateral force onto an IOL 70, and thereby guide the IOL 70 to adopt a compressed configuration.

Furthermore, in some implementations, for example as shown in FIG. 10B, the plunger tip 220 is adapted to contact the IOL 70 following at least partial compression of the IOL 70 by the compression arms 1. In some implementations, the plunger tip 220 is adapted to contact the IOL 70 in response to the IOL 70 adopting the compressed configuration.

In various implementations, the plunger 30 may be disposed within an IOL injector 10. For example, FIG. 10A-FIG. 10B are schematics of an example plunger 30 having IOL compression arms 1, and an IOL 70, such as an IOL base 461, disposed within an IOL injector 10. The example IOL injector 10 of FIG. 10A-FIG. 10B has an injector body 20 that includes a main body 21 having a proximal end 50 and a distal end 23. The example IOL injector 10 also has a nozzle 25 having a proximal end 22 and a distal end 60, the proximal end 22 of the nozzle 25 coupled to the distal end 23 of the main body 21, the nozzle 25 further having an IOL storage location 80 configured to house an uncompressed IOL 70, and an IOL dwell location 809 distal to the IOL storage location 80. The example IOL injector 10 also has a bore 40 having a longitudinal axis 75 extending from the proximal end 50 of the main body 21 to the distal end 60 of the nozzle 25, wherein a distal portion of the bore 40 within the nozzle 25 forms a tapered delivery channel 31. The plunger is movably coupled within the injector body 20 and aligned within the bore 40.

FIG. 10A is a schematic of an example plunger having IOL compression arms in an initial compression arm configuration, and an uncompressed IOL 70. FIG. 10B is a schematic of an example plunger having IOL compression arms in a second compression arm configuration, and a compressed IOL 70.

As shown for example in FIG. 10A-FIG. 10B, in response to an axial movement of the plunger 30, in some implementations, each of the compression arms 1 are adapted to move axially and contact an internal lateral surface 64 of the tapered delivery channel 31. In response, the compression arms 1 are adapted to flex toward one another to adopt a second compression arm 1 configuration wherein the compression arms 1 are adapted to apply an inward lateral force onto an IOL 70, and thereby guide an IOL 70 to adopt a compressed configuration.

Accordingly, following the compression of the IOL 70 under control of the IOL compression arms, the plunger 30 may then be further advanced axially such that the plunger tip 220 longitudinally displaces the compressed IOL 70 and advances the compressed IOL 70 axially through the delivery passage and through the opening 29 at the distal end 60 of the nozzle 25.

Figure 11:
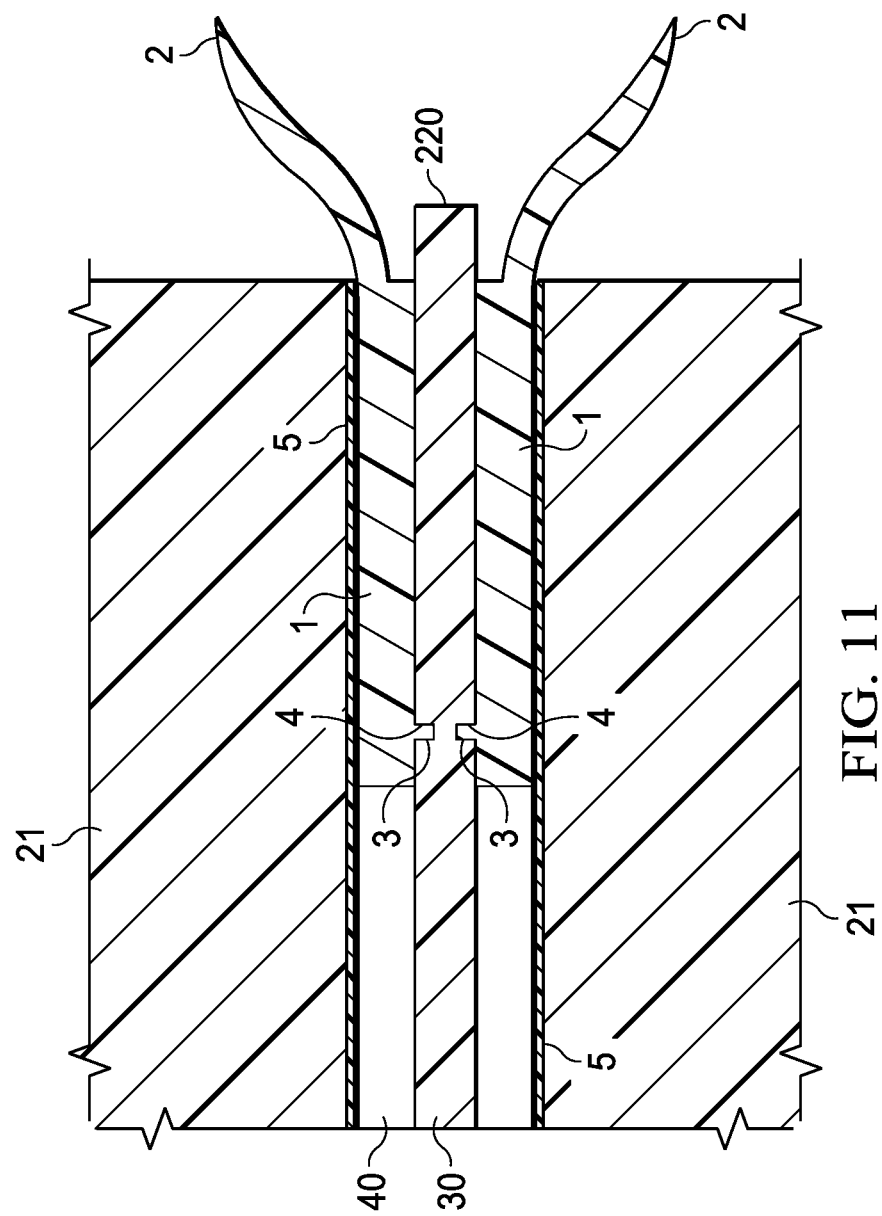
FIG. 11 is another schematic of an example plunger having IOL compression arms, disposed within an IOL injector.

FIG. 11 is another schematic of an example plunger having IOL compression arms, in which the compression arms 1 are configured to be decoupled from the plunger 30, such as decoupled from the plunger rod 210. Typically, in some implementations, the delivery channel 31 may not be sized to allow axial movement of the compressed IOL together with the compression arms through the delivery channel 31 to the distal end 60 of the nozzle 25. Further, it will be understood that typically the compressed IOL 70 does not require ongoing contact with the compression arms after the IOL 70 has adopted the compressed configuration within the tapered delivery channel 31 and may instead be maintained in a compressed configuration by contact with the inner surface 64 of the tapered delivery channel 31 while being axially advanced through the delivery channel in contact with the plunger tip 220 to the distal end 60 of the nozzle 25.

Accordingly, in some implementations, the compression arms 1 are configured to be decoupled from the plunger 30 in response to the compression arms 1 adopting the second configuration. In response to decoupling, upon further axial movement of the plunger 30, the compression arms 1 are adapted not to further move axially within the delivery channel 31, and the plunger tip 220 is adapted to axially push a compressed IOL through the delivery channel 31.

In some implementations, such as shown in FIG. 11, the proximal ends of the compression arms 1 may each include a pin 3, and the plunger 30 may have a hole 4 adapted to receive the pins, thereby coupling the compression arms 1 to the plunger 30. In some implementations, in order to maintain coupling of the plunger 30 to the compression arms 1 until the compression arms 1 adopt the second compression arm configuration, a portion of the bore 40 within the injector body 20 may be sized to maintain contact between the plunger 30 and the compression arms 1. For example, as shown in FIG. 11, a portion of the distal end of the main body 21 may include a sleeve 5 having a bore 40 diameter sized such that the pins are disposed within the hole 4 when the proximal ends of the compression arms 1 axially are disposed within the sleeve 5. Upon further axial movement of the plunger 30, in response to the compression arms 1 moving from the initial compression arm 1 configuration to the second compression arm 1 configuration, the proximal ends of the compression arms 1 may be configured to exit the sleeve 5 and in response are adapted to flex outward away from the plunger 30, thereby removing the pins 3 from the hole 4 and decoupling the compression arms 1 from the plunger 30. Accordingly, the plunger 30, such as the plunger rod, including the plunger tip 220, but not the compression arms 1, may then move further axially within the nozzle, thereby advancing the IOL 70 to the distal end 60 of the nozzle 25.

Figure 12:
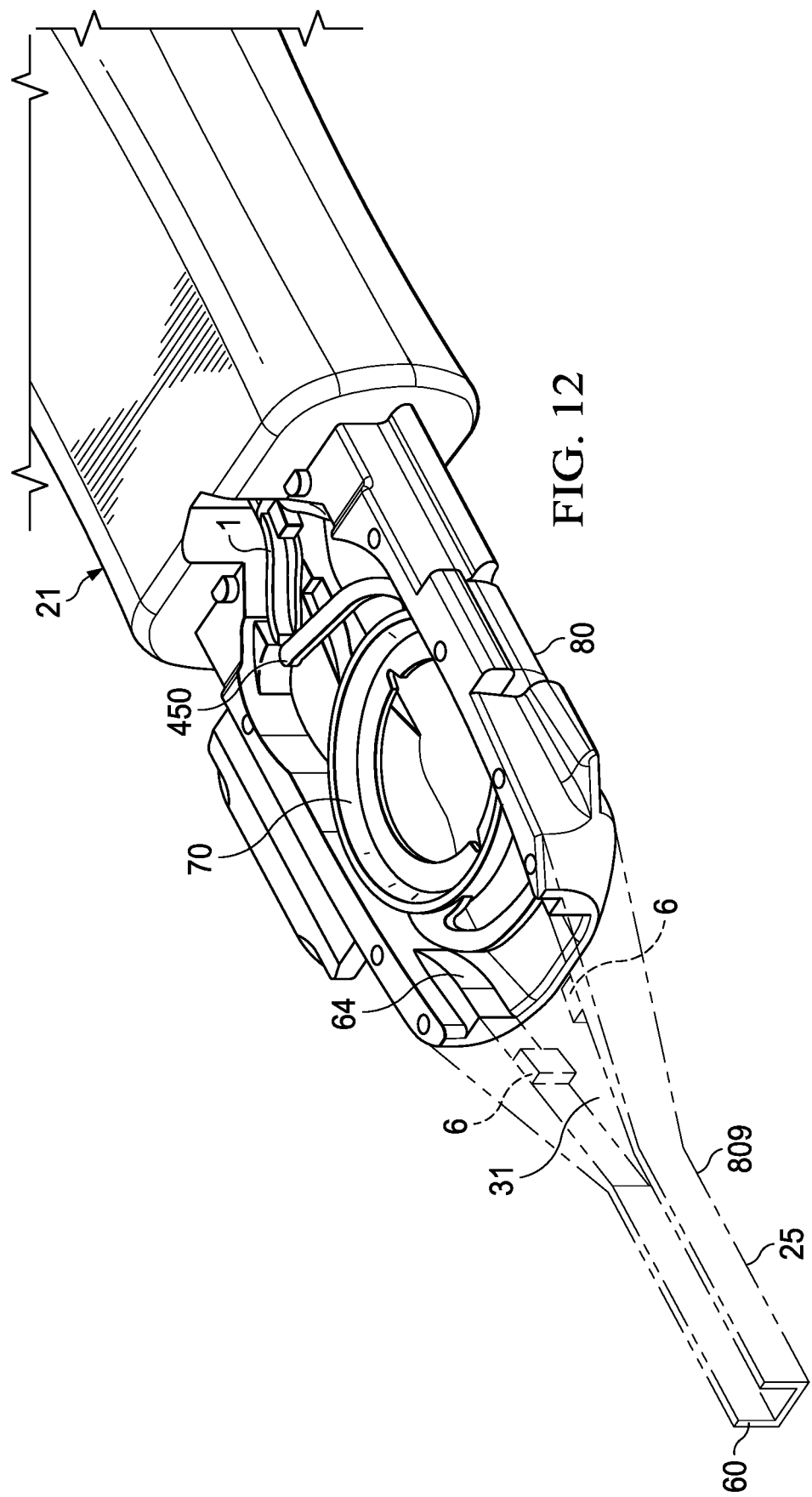
FIG. 12 is a perspective view of an example IOL injector including a plunger having IOL compression arms and a nozzle having hard stops.

In some implementations, for example as shown in FIG. 12, the delivery channel 31 may include a hard stop 6 adapted to contact the compression arm tips 2, such as when the compression arms 1 are in the second compression arm configuration, and prevent the decoupled compression arms 1 from further axially moving through the delivery channel 31, while allowing a decoupled plunger 30, such as the plunger rod 210 including the plunger tip 220, to move further axially in response to further axial force applied to the plunger 30.

Figure 13:
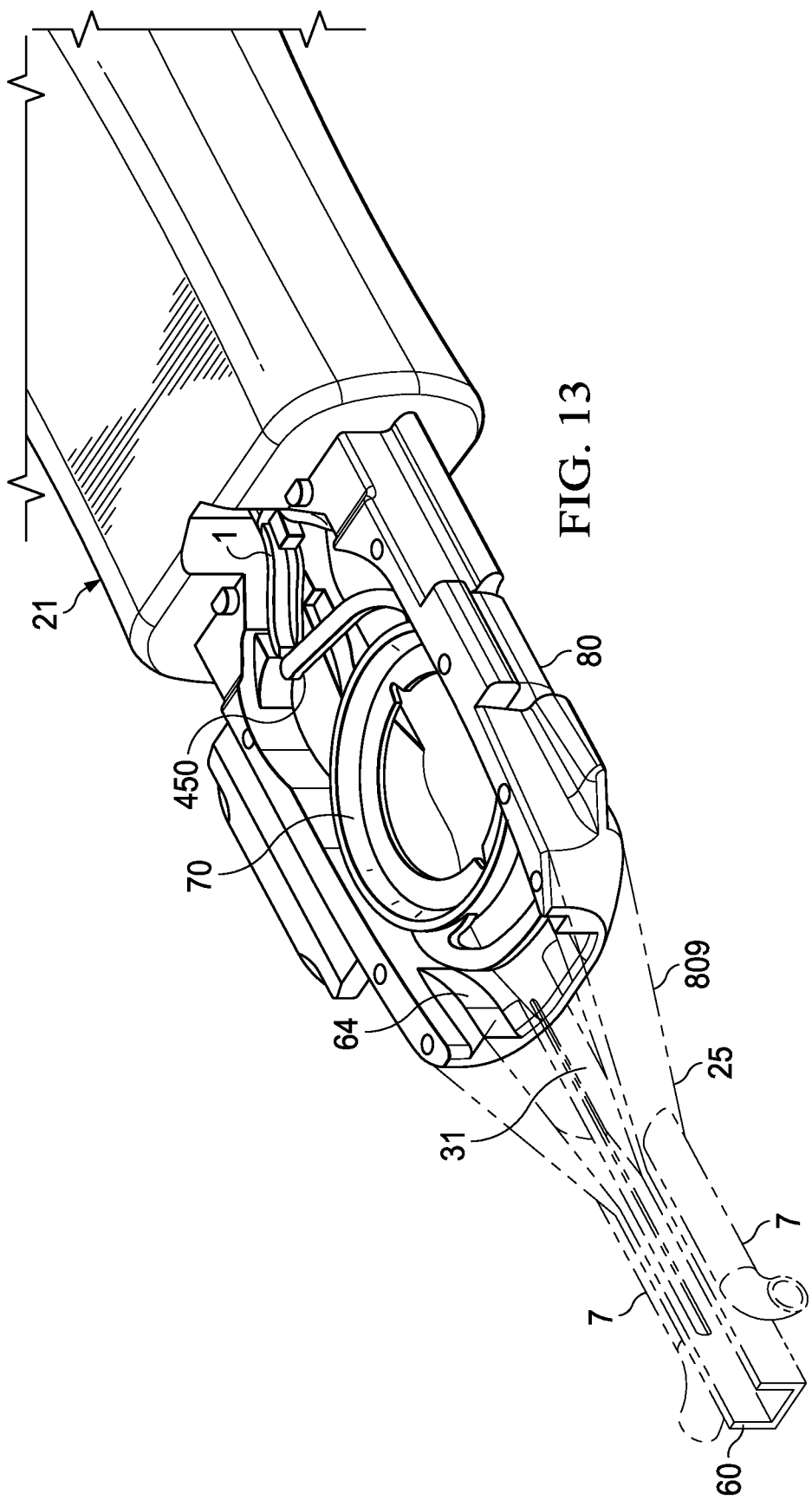
FIG. 13 is a perspective view of an example IOL injector including a plunger having IOL compression arms and a nozzle having channels adapted to receive the compression arms.

In some implementations, for example as shown in FIG. 13, the nozzle 25 may include a cutout or relief feature, or, for example channels 7 disposed longitudinally within the nozzle 25 and adapted to receive the compression arms 1. For example, in response to further axial movement of the plunger 30 following compression of the IOL 70, such as when the compression arms 1 are in the second compression arm configuration, at least a portion of the compression arms 1 are configured to be decoupled from the plunger 30, such as decoupled from the plunger rod 210, such that the plunger rod 210 including the plunger tip 220 is adapted to axially move through the delivery channel 31, and the compression arms 1 are adapted to enter and axially slide through the channels 7.

In some implementations, the plunger 30 of the present disclosure may be configured such that the IOL 70 may be in the IOL storage location 80 when the compression arms 1 are in the initial compression arm configuration, and the IOL 70 may be in the dwell location 809 when the compression arms 1 are in the second compression arm configuration.

Figure 14:
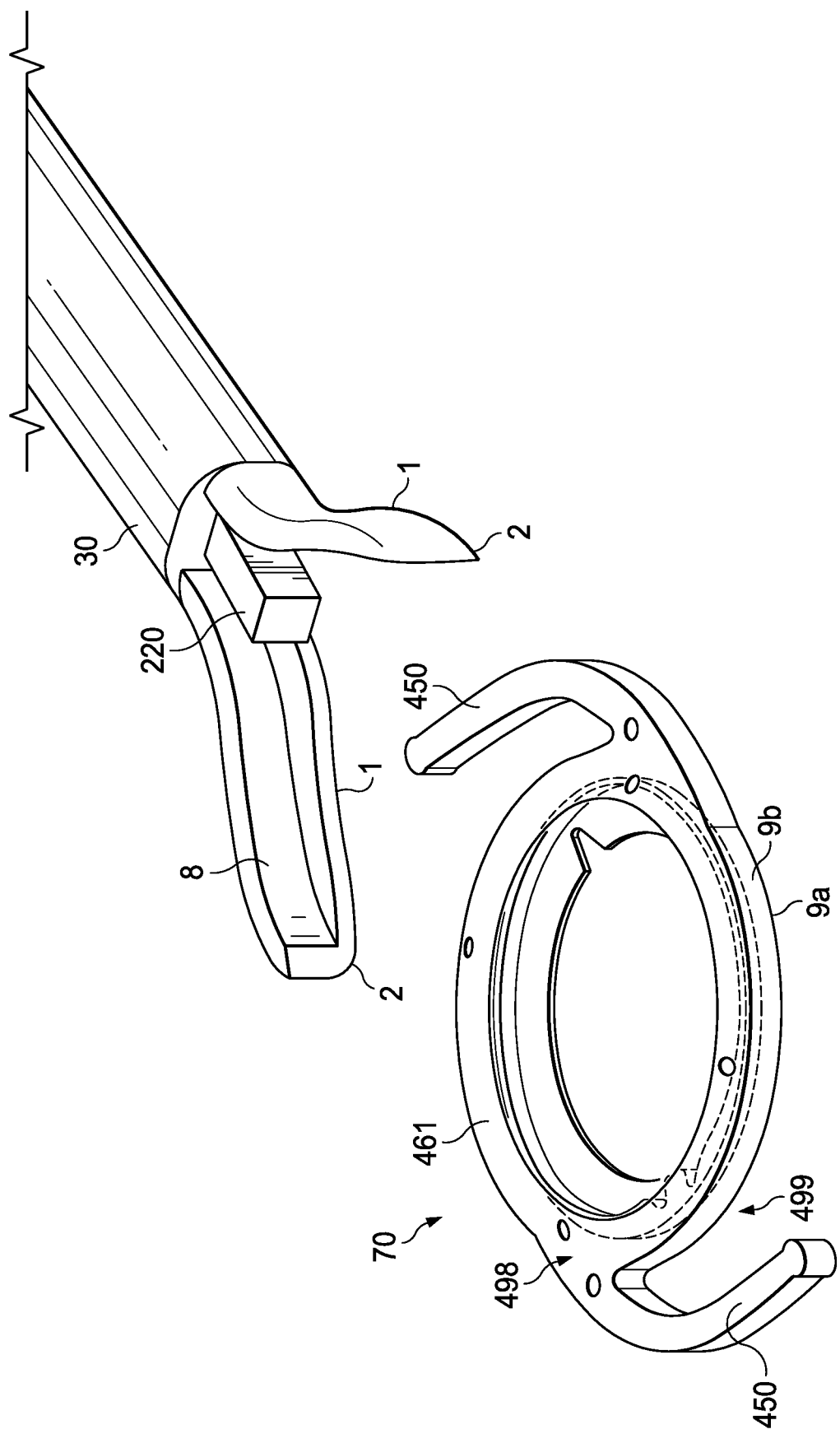
FIG. 14 is a detail view of an example plunger having IOL compression arms and an IOL base.

The compression arms 1 of the plunger 30 may be shaped to provide optimal contact surface area with the IOL 70. In some implementations, for example as shown in FIG. 14, the compression arms 1 may have a concave inner surface 8 adapted to contact a lateral outer edge 9a of an IOL 70 and a lower outer edge 9b of an IOL 70.

In some implementations, the IOL injector 10 of the present disclosure may include a plunger 30 having compression arms 1 adapted to separately inject an IOL base 461, an IOL optic 460, or both. In some implementations, the IOL injector 10 of the present disclosure may include a plunger 30 having compression arms 1 adapted to concurrently inject an IOL base 461 and an IOL optic 460.

Non-limiting examples of IOL injectors that may be adapted according to the present disclosure include those described in U.S. Pat. No. 7,156,854 and U.S. Patent Application Publication No. 2016/0256316, the disclosures of each being incorporated herein by reference in their entireties.

The above disclosed subject matter is to be considered illustrative, and not restrictive, and the appended claims are intended to cover all such modifications, enhancements, and other implementations which fall within the true spirit and scope of the present disclosure. Thus, to the maximum extent allowed by law, the scope of the present disclosure is to be determined by the broadest permissible interpretation of the following claims and their equivalents and shall not be restricted or limited by the foregoing detailed description.

The invention claimed is:

1. An intraocular lens (IOL) injector plunger comprising:
a plunger tip formed at a distal end of the plunger and adapted to contact an IOL and axially move the IOL in response to an axial force applied to the plunger; and
a first and a second flexible IOL compression arm disposed on opposite lateral sides of the distal end of the plunger, each flexible IOL compression arm having a proximal end coupled to the plunger, and a tapered distal end forming a compression arm tip, wherein:
the plunger is movably coupled within an injector body of an IOL injector, the injector body comprising a tapered delivery channel;
in an initial compression arm configuration, the first and second flexible IOL compression arms are laterally splayed such that the compression arm tip of the first flexible IOL compression arm is adapted to contact a first end of a proximal haptic of an uncompressed IOL, the first end comprising a haptic tip of the proximal haptic, and a the compression arm tip of the second flexible IOL compression arm is adapted to contact a second end of a proximal haptic of an uncompressed IOL;
in response to inward lateral forces applied to outer lateral surfaces of the first and second flexible IOL compression arms, the first and second flexible IOL compression arms are adapted to flex toward one another to adopt a second compression arm configuration wherein the first and second flexible IOL compression arms are adapted to apply an inward lateral force onto the IOL, and thereby guide the IOL to adopt a compressed configuration; and
the first and second flexible IOL compression arms are configured to be decoupled from the plunger in response to the first and second flexible IOL compression arms adopting the second compression arm configuration, such that in response to decoupling, upon axial movement of the plunger:
the first and second flexible IOL compression arms are adapted not to move axially within the delivery channel; and
the plunger tip is adapted to axially push a compressed IOL through the delivery channel.

2. The plunger of claim 1, wherein:
the plunger tip is adapted to contact the IOL in response to the IOL adopting the compressed configuration.

3. The plunger of claim 1, wherein the injector body comprises:
a main body having a proximal end and a distal end;
a nozzle having a proximal end and a distal end, the proximal end of the nozzle coupled to the distal end of the main body, the nozzle further having an IOL storage location configured to house an uncompressed IOL, and an IOL dwell location distal to the IOL storage location; and
a bore having a longitudinal axis extending from the proximal end of the main body to the distal end of the nozzle, wherein a distal portion of the bore within the nozzle forms the tapered delivery channel;
wherein:
the plunger is aligned within the bore; and
in response to an axial movement of the plunger, each of the first and second flexible IOL compression arms are adapted to move axially and contact an internal lateral surface of the tapered delivery channel, and in response, the first and second flexible IOL compression arms are adapted to flex toward one another to adopt the second compression arm configuration.

4. The plunger of claim 1, wherein:
the proximal ends of the first and second flexible IOL compression arms each comprise a pin;
the plunger comprises a hole adapted to receive the pins, thereby coupling the first and second flexible IOL compression arms to the plunger; and
a portion of the distal end of the main body comprises a sleeve having a bore sized such that the pins are adapted to be disposed within the hole when the proximal ends of the first and second flexible IOL compression arms axially are disposed within the sleeve;
wherein the first and second flexible IOL compression arms are adapted such that, in response to the first and second flexible IOL compression arms moving from the initial compression arm configuration to the second compression arm configuration:
the proximal ends of the first and second flexible IOL compression arms are adapted to exit the sleeve and in response are adapted to flex outward away from the plunger, thereby removing the pins from the hole and decoupling the first and second flexible IOL compression arms from the plunger.

5. The plunger of claim 1, wherein:
the delivery channel comprises a hard stop adapted to contact the compression arm tips and prevent the first and second flexible IOL compression arms from further axially moving through the delivery channel after decoupling.

6. The plunger of claim 3, wherein:
the nozzle further comprises channels disposed longitudinally within the nozzle and adapted to receive the first and second flexible IOL compression arms;
wherein in response to further axial movement of the plunger following compression of the IOL:
a portion of the first and second flexible IOL compression arms are configured to be decoupled from the plunger such that the plunger tip is adapted to further axially move through the delivery channel; and
the first and second flexible IOL compression arms are adapted to axially slide through the channels.

7. The plunger of claim 3, wherein the plunger is configured such that:
the IOL is in the IOL storage location when the first and second flexible IOL compression arms are in the initial compression arm configuration; and
the IOL is in the IOL dwell location when the first and second flexible IOL compression arms are in the second compression arm configuration.

8. The plunger of claim 1, wherein:
the first and second flexible IOL compression arms have a concave inner surface adapted to contact a lateral outer edge of the IOL and a lower outer edge of the IOL.

9. The plunger of claim 1, wherein:
the IOL injector is adapted to separately inject an IOL base, an IOL optic, or both.

10. The plunger of claim 1, wherein:
the IOL injector is adapted to concurrently inject an IOL base and an IOL optic.

11. An intraocular lens (IOL) injector plunger comprising:
a plunger tip formed at a distal end of the plunger and adapted to contact an IOL and axially move the IOL in response to an axial force applied to the plunger; and
a first and a second flexible IOL compression arm disposed on opposite lateral sides of the distal end of the plunger, each flexible IOL compression arm having a proximal end coupled to the plunger, and a tapered distal end forming a compression arm tip, wherein:
  the plunger is movably coupled within an injector body of an IOL injector, the injector body comprising a nozzle and a tapered delivery channel, the nozzle comprising channels disposed longitudinally within the nozzle and adapted to receive the first and a second flexible IOL compression arms;
  in an initial compression arm configuration, the first and second flexible IOL compression arms are laterally splayed such that the compression arm tip of the first flexible IOL compression arm is adapted to contact a first end of a proximal haptic of an uncompressed IOL, the first end comprising a haptic tip of the proximal haptic, and the compression arm tip of the second flexible IOL compression arm is adapted to contact a second end of a proximal haptic of an uncompressed IOL;
  in response to inward lateral forces applied to outer lateral surfaces of the first and second flexible IOL compression arms, the first and second flexible IOL compression arms are adapted to flex toward one another to adopt a second compression arm configuration wherein the first and second flexible IOL compression arms are adapted to apply an inward lateral force onto the IOL, and thereby guide the IOL to adopt a compressed configuration; and
  in response to axial movement of the plunger following compression of the IOL:
    a portion of each of the first and second flexible IOL compression arms are configured to be decoupled from the plunger such that the plunger tip is adapted to axially move through the delivery channel; and
    the first and second flexible IOL compression arms are adapted to axially slide through the channels of the nozzle.

* * * * *